United States Patent
Sato et al.

(10) Patent No.: US 9,539,185 B2
(45) Date of Patent: Jan. 10, 2017

(54) SELF-FOAMING CLEANSING SYSTEM

(71) Applicant: L'OREAL, Paris (FR)

(72) Inventors: Bruno Sato, Suzano (BR); Jaimie Mecca, Clifton, NJ (US); Pedro Aprigliano Fernandes, Rio de Janeiro (BR); Megumi Nishitani Yukuyama, Sao Paulo (BR)

(73) Assignee: L'OREAL, Paris (FR)

( * ) Notice: Subject to any disclaimer, the term of this patent is extended or adjusted under 35 U.S.C. 154(b) by 354 days.

(21) Appl. No.: 14/041,288

(22) Filed: Sep. 30, 2013

(65) Prior Publication Data
US 2015/0093348 A1   Apr. 2, 2015

(51) Int. Cl.
*A61K 8/06* (2006.01)
*A61Q 5/02* (2006.01)

(52) U.S. Cl.
CPC ............. *A61K 8/062* (2013.01); *A61Q 5/02* (2013.01)

(58) Field of Classification Search
None
See application file for complete search history.

(56) References Cited

U.S. PATENT DOCUMENTS

| | | | |
|---|---|---|---|
| 6,723,688 B1 | 4/2004 | Malik et al. | |
| 7,316,808 B2 | 1/2008 | Candau | |
| 2002/0012680 A1* | 1/2002 | Patel | A61K 9/4808 424/400 |
| 2006/0217283 A1 | 9/2006 | De Salvert et al. | |
| 2008/0286367 A1* | 11/2008 | SenGupta | A61K 8/26 424/489 |
| 2012/0157366 A1 | 6/2012 | Anim-Danso et al. | |
| 2012/0308492 A1 | 12/2012 | Allef et al. | |

FOREIGN PATENT DOCUMENTS

WO   2013045626 A1   4/2013

OTHER PUBLICATIONS

HLB System (The HLB system. A time-saving guide to Emulsifier Selection (Pub: ICI Americas Inc., 1980).*
SALAGER (Surfactants types and Uses (2002)).*

\* cited by examiner

*Primary Examiner* — Jake Vu
(74) *Attorney, Agent, or Firm* — Polsinelli PC

(57) ABSTRACT

A self-foaming cleansing composition is described, said composition comprising at least one high HLB surfactant and at least one low HLB surfactant, wherein ratio of the high HLB surfactant to the low HLB surfactant is from about 2:1 to about 4:1.

5 Claims, No Drawings

SELF-FOAMING CLEANSING SYSTEM

TECHNICAL FIELD

The present invention relates to an essentially sulfate-free self-foaming cleansing system that is devoid of parabens and silicon. This system includes and oil-in-water (O/W) emulsion comprising at least one high HLB surfactant and at least one low HLB surfactant wherein ratio of the high HLB surfactant to the low HLB surfactant is from about 2:1 to about 4:1. This system is particularly useful in self-foaming shampoos.

BACKGROUND OF THE INVENTION

Foaming cosmetic products are currently popular. For environmental reasons, it is preferred that these products use air propulsion for delivery of the foam as opposed to more typical propellant gases. Air propelled containers which may be used to deliver foaming cosmetic products include for example a foaming device sold by Airspray/REXAM PLC. These foaming products may be used for personal cleansing, including as shampoos.

Micro emulsions can be used to produce foamable formulations. For example, US2006/0217283 (L'Oreal) describes foam compositions in the form of O/W emulsions useful in cosmetics and dermatology. US2012/0308492 describes a foamable O/W emulsion that does not comprise a propellant gas and which can be used for personal care products.

Traditional shampoos have relatively high viscosities which makes it difficult to distribute evenly with certain hair types, for example thick hair and/or curly hair and/or dry hair. For thick, curly hair in particular, traditional shampoos/conditioning systems are not only hard to apply, they are hard to rinse off, often yielding dull hair and loss of curl definition.

In contrast, the current invention provides a sulfate free surfactant-based cleansing system that is deliverable in a self-foaming container and has relatively low viscosity thus spreading evenly and easily on thick and/or curly hair and/or dry hair. Inasmuch as the cleansing system of the invention is easily risible it also maximizes the definition and shine of the hair without unduly weighing. The system meanwhile also provides excellent foam and efficiently and thoroughly cleans and conditions thick/wavy/dray hair.

BRIEF SUMMARY OF THE INVENTION

The present invention relates to an oil-in-water emulsion comprising:
(1) an oil phase comprising
   (a) from about 1.6% to about 3% of an emulsifying surfactant composition having (i) from about 1.3% to about 2% of one or more high HLB surfactant and (ii) from about 0.3% to about 1.0% of one or more low HLB surfactant, wherein the ratio of the high HLB surfactant to the low HLB surfactant is between about 2:1 to about 4:1; and
   (b) from about 0.01% to about 1% of one or more non silicone fatty compound; and
(2) an aqueous phase comprising
   (c) from about 3.4% to about 7.4% of one or more amphoteric surfactant;
   (d) from about 1.3% to about 2.7% of one or more sulfate-free anionic surfactants;
   (e) from about 0.05% to about 0.6% of one or more cationic polymer; and
   (f) from about 60% to about 95% water;
   wherein the oil phase is dispersed in the aqueous phase (O/W); said emulsion having a viscosity from about 10 cP to about 30 cP; and wherein all weights are relative to the total weight of the emulsion.

The emulsion optionally may include other components appropriate for the emulsion's intended end use, such as for example additional anionic surfactants, additives to modulate freezing point, pigments, preservatives, and the like.

The invention also provides a method of cleansing and conditioning hair comprising contacting the hair with the above-described composition.

DETAILED DESCRIPTION OF THE INVENTION

The present invention provides self-foaming compositions that are stable for three months at a temperatures ranging from 4° C. to 40° C. A further advantage is that the foam can be produced without synthetic propellant gases and there is also no need for shaking the storage container. An additional advantage of the claimed O/W emulsions of the invention is that they provide good foam even with very small amounts of surfactants. This is desirable as some surfactants can cause skin irritation. The O/W emulsions of the invention are preferably used in self-foaming shampoos. These shampoos provide good conditioning, shine and body. The shampoos of the invention are especially useful for curly hair affording good curl definition.

Definitions

"Aqueous phase" means the phase comprising water as well as such substances of a formulation which, due to their hydrophilic character, can be mixed and/or dissolved and/or dispersed in water. Thus, such substances that may be found in the aqueous phase include glycols, for instance propylene glycol and glycerol; monoalcohols such as ethanol, propanol, butanol; isopropanol, and isobutanol; polyquaternium, such as polyquaternium-7 and 10; salts; and water-soluble additives "Clear" as used herein means that the composition is visually clear. More specifically, clarity of a formulation is measured by the transmittance percentage of light with a wavelength of 700 nm by UV-Visible spectrophotometry. "Clear" samples allow for between 90% and 100% of the light to pass through the formula.

"cP" means centipoise, a centimeter-gram-second unit of viscosity that is equal to 1/100 of a poise.

"Emulsifier or emulsifying surfactant" is a term of art that is well known to those skilled in the art. See, e.g. http://pharmlabs.unc.edu/labs/emulsions/agents.htm. It is a compound that has a hydrophilic part and a lipophilic part ("amphiphilic) and facilitates the dispersion of two mutually insoluble phases, in this case the oil and water phases, assisting in the formation of the O/W emulsion. Such compounds do not have an overall electric charge in their working environment (are "non-ionic").

"Foamability" means the ability of a composition to produce foam. Both the amount and stability of the foam are measures of foamability.

"HLB" as used herein means the hydrophilic-lipophilic balance of a molecule, e.g. an emulsifier. It is the ratio between the hydrophilic part and lipophilic part of a molecule. This term is well known to those skilled in the art. See, e.g., "The HLB system. A time-saving guide to Emulsifier Selection" (Pub: ICI Americas Inc., 1984) and US2006/0217283 at [0053]. "High HLB" for an emulsifying surfactant in an O/W emulsion of the invention means an HLB of equal to greater than about 15. "Low HLB" for an emulsifying surfactant for an O/W emulsion of the invention means an HLB less than about 15.

"Oil phase" or "oily phase" means the phase containing the lipophilic, non-ionic compounds, which in the current invention are typically oils (lipophilic constituents that are liquid at room temperature). They are for example triglycerides, hydrocarbons, esters and other fatty substances as herein described, and any lipophilic additive that may be present. The oil phase does not include the charged surfactants.

"One or more" as used herein includes individual components as well as mixtures/combinations.

"Stable" means that the ability of the emulsion to foam (also referred to a "foamability") is relatively unchanged and there is no discernible sign of instability such as separation of the phases.

"Self-foaming" means that the composition foams once delivered through the air-propelled foaming applicator and does not need additional shaking of the applicator or rubbing of the composition between the hands.

The term "essentially sulfate free" means that, while it is preferable that no sulfate is present in the compositions or emulsions of the invention, it is possible to have very small amounts of sulfate in the compositions, provided that these amounts do not materially affect the advantageous properties of the composition. In particular, "essentially sulfate-free anionic surfactant" means that no traditional sulfate-based anionic surfactants are used in the composition and that the surfactant does not contribute sulfate to the composition. Most preferably, the compositions contain no sulfate. To the extent any sulfate is present in the compositions, it is present at an amount of less than about 2.0% by weight, typically less than about 1.5% by weight, typically less than about 1.0% by weight, typically less than about 0.5% by weight, more typically less than about 0.1% by weight, based on the total weight of the composition. To the extent present, the sulfates in such compositions are typically contributed by components other than the anionic surfactant.

The O/W emulsions according to the invention comprise an oil phase (or lipophilic phase) dispersed in an aqueous phase. The oil phase is present in an amount ranging from about 2.1% to about 4%, preferably from about 2% to about 3%, most preferably about 2.4%, including all ranges and subranges therebetween, by weight relative to the total weight of the composition. The aqueous phase is present in an amount ranging from about 96% to about 99%, preferably from about 97% to about 98%, most preferably about 97.6%, including all ranges and subranges therebetween, by weight relative to the total weight of the composition.

The emulsions obtained according to the invention are clear, signifying that the oils are properly solubilized.

The viscosity of the emulsions of the composition, measured at 25° C. with a Rheomat 180 viscometer at 100 rpm (revolutions per minute) using a No. 1 spindle is preferably greater than or equal to 10 cP, typically from 10 to about 30 cP, most typically from about 15 to about 25 cP, preferably from about 18 to about 23 cP, most preferably at about 22 cP, including all ranges and subranges therebetween. The viscosity is generally measured 10 minutes after switching on the rotation of the spindle.

The pH of the emulsions of the invention ranges from about 4.0 to about 6.0, more preferably from about 5.0 to about 5.6, most preferably about 5.2, including all ranges and subranges therebetween.

In an embodiment, the present invention relates to a compositions comprising:
 (a) from about 1.6% to about 3% of an emulsifying surfactant composition having (i) from about 1.3% to about 2% of one or more high HLB surfactant and (ii) from about 0.3% to about 1.0% of one or more low HLB surfactant, wherein the ratio of the high HLB surfactant to the low HLB surfactant is between about 2:1 to about 4:1;
 (b) from about 0.01% to about 1% of one or more non-silicone fatty compound;
 (c) from about 3.4% to about 7.4% of one or more amphoteric surfactant;
 (d) from about 1.3% to about 2.7% of one or more sulfate-free anionic surfactants;
 (e) from about 0.05% to about 0.6% of one or more cationic polymer; and
 (f) from about 60% to about 95% water;
 said composition having a viscosity from about 10 cP to about 30 cP; and wherein all weights are relative to the total weight of the emulsion.

The compositions optionally may include other components appropriate for the emulsion's intended end use, such as for example additional anionic surfactants, additives to modulate freezing point, pigments, preservatives, and the like.

In an embodiment, the invention relates to an oil-in-water emulsion comprising:
 (1) an oil phase comprising
  (a) from about 1.6% to about 3% of an emulsifying surfactant composition having (i) from about 1.3% to about 2% of one or more high HLB surfactants and (ii) from about 0.3% to about 1.0% of one or more of a low HLB surfactant, wherein the ratio of the high HLB surfactant to the low HLB surfactant is between about 2:1 to about 4:1; and
  (b) from about 0.01% to about 1% of one or more non-silicone fatty compound; and
 (2) an aqueous phase comprising
  (c) from about 3.4% to about 7.4% of one or more amphoteric surfactant;
  (d) from about 1.3% to about 2.7% of one or more sulfate-free anionic surfactants;
  (e) from about 0.05% to about 0.6% of one or more cationic surfactants; and
  (f) from about 60% to about 95% water;
 said emulsion having a viscosity from about 10 cP to about 30 cP; wherein the oil phase is dispersed in the aqueous phase and wherein all weights are relative to the total weight of the emulsion.

The emulsion optionally may include other components appropriate for the emulsion's intended end use, such as for example additional anionic surfactants, additives to modulate freezing point, pigments, preservatives, and the like.

In a preferred embodiment, the invention relates to an oil-in-water emulsion comprising:
 (1) an oil phase comprising
  (a) from about 1.6% to about 3% of a non-ionic emulsifying surfactant composition having (i) from about 1.3% to about 2% of one or more high HLB surfactants and (ii) from about 0.3% to about 1.0% of one or more of a low HLB surfactant, wherein the ratio of the high HLB surfactant to the low HLB surfactant is between about 2:1 to about 4:1; and
  (b) from about 0.01% to about 1% of one or more non-silicone fatty compound; and
 (2) an aqueous phase comprising
  (c) from about 3.4% to about 7.4% of one or more amphoteric surfactant;

(d) from about 1.3% to about 2.7% of one or more sulfate-free anionic surfactants;
(e) from about 0.05% to about 0.6% of one or more cationic surfactants;
(f) from about 60% to about 95% water; and
(g) from about 0.004% to about 20% of one of more additives;

said emulsion having a viscosity from about 10 cP to about 30 cP; wherein the oily phase is dispersed in the aqueous phase and wherein all weights are relative to the total weight of the emulsion.

In another preferred embodiment, the invention relates to a self-foaming oil-in-water emulsion comprising:
(1) an oil phase comprising
  (a) from about 1.6% to about 3% of an emulsifying surfactant composition having (i) from about 1.3% to about 2% of a high HLB non-ionic surfactant and (ii) from about 0.3% to about 1.0% of a low HLB non-ionic surfactant, wherein the ratio of the high HLB surfactant to the low HLB surfactant is between about 2:1 to about 4:1; and
  (b) from about 0.01% to about 1% of one or more non-silicone fatty compound; and
(2) an aqueous phase comprising
  (c) from about 3.4% to about 7.4% of an amphoteric surfactant;
  (d) from about 1.3% to about 2.7% of two or more sulfate-free anionic surfactants;
  (e) from about 0.05% to about 0.6% of two cationic surfactants;
  (f) from about 60% to about 95% water; and
  (g) from about 0.004% to about 20% of one of more additives;

said emulsion having a viscosity from about 10 cP to about 30 cP; wherein the oily phase is dispersed in the aqueous phase and wherein all weights are relative to the total weight of the emulsion.

Emulsifying Surfactant Composition (Component (a))

The emulsions of the invention include an emulsifying surfactant composition. The emulsifying surfactant composition typically is non-ionic and comprises one or more high HLB, preferably non-ionic, surfactant (component (a)(i)), and one or more low HLB, preferably non-ionic, surfactant (component (a)(ii)).

In an embodiment, the high HLB non-ionic surfactant may be selected, for example, from PEG-40 hydrogenated castor oil, PEG-60 hydrogenated castor oil, PEG-25 hydrogenated castor oil, and mixtures thereof. More particularly, the high HLB non-ionic surfactant is PEG-40 hydrogenated castor oil.

The high HLB non-ionic surfactant is present in an amount from about 1.3% to about 2%, preferably from about 1.3 to about 1.7, most preferably about 1.5%, including all ranges and subranges therebetween, by weight relative to the total weight of the emulsion.

The emulsions of the invention also include one or more low HLB non-ionic surfactant. In an embodiment, the low HLB surfactant is selected, for example, from sorbitan oleate, lecithin, sorbitan, monostearate, sorbitan isostearate, sorbitan stearate, oleth-2, sorbitan sesquioleate, and mixtures thereof. Preferably the low HLB non-ionic surfactant is selected from sorbitan oleate, lecithin and sorbitan monostearate, and mixtures thereof. More particularly the low HLB non-ionic surfactant is sorbitan oleate.

The low HLB non-ionic surfactant is present in an amount from about 0.3% to about 1%, preferably from about 0.4% to about 0.8%, most preferably about 0.5%, including all ranges and subranges therebetween, by weight relative to the total weight of the emulsion.

The ratio of the high HLB surfactant to low HLB surfactant is from about 2:1 to about 4:1, preferably about 3:1, including all ranges and subranges therebetween.

The non-ionic surfactant system is present in the emulsion in an amount from about 1.6% to about 3%, preferably from about 1.7% to about 2.5%, most preferably about 2%, including all ranges and subranges therebetween, by weight relative to the total weight of the emulsion.

Non-Silicone Fat(s) (Component (b))

The emulsions of the invention include one or more non-silicone fat that is hydrocarbon-based, preferably selected from plant oils. Useful plant oils include olive oil, coconut oil, avocado oil, apricot oil, sweet almond oil, castor oil, coriander oil, grapeseed oil, rapeseed oil, hazelnut oil, Shea butter, palm oil, apricot kernel oil, rice ban oil, corn germ oil, wheatgerm oil, soybean oil, sunflower oil, evening primrose oil, safflower oil, sesame seed oil, passionflower oil, camellia oil, and mixtures thereof. Preferably, the oils are selected from olive oil, coconut oil, avocado oil, and mixtures thereof.

While oils of plant origin are preferred, other hydrocarbon-based oils of mineral or synthetic origin are also useful. Such oils include, for example, volatile or non-volatile liquid paraffins and derivatives thereof, petroleum jelly, mineral oil, perhydrosqualene, polydecenes, isohexadecane, isododecane, and hydrogenated polyisobutene such as Paream™ oil (sold by NOF Corp.), and mixtures thereof.

Other non-silicone fats useful in the invention include, for example, esters and carbonates, as well as triglycerides. Examples of useful esters include C12-15 alkyl benzoate, cetearyl isononanoate, cetyl ethylhexanoate, coco-caprylate/caprate, decyl oleate, ethylhexyl stearate, hexyl laurate, isopropyl myristate, isopropyl palmitate, oleyl erucate, and mixtures thereof.

Examples of carbonates include dicaprylyl ether (available as Cetiol OE from Cognis) and dicaprylyl carbonate (Cetiol CC also from Cognis), Examples of tryglicerides include caprylic/capric triglyceride (sold by Cremer Oleo GmbH & Co. as MIGLYOL® 810 and 812) and caprylic/capric linoleic triglyceride (sold by Cremer Oleo GmbH & Co. as MIGLYOL® 818 and 829), and mixtures thereof.

The fat component is present in the emulsion in an amount from about 0.01% to about 1%, preferably from about 0.05 to about 0.7%, most preferably about 0.4%, including all ranges and subranges therebetween, by weight relative to the total weight of the emulsion.

In a particularly preferred embodiment the ratio of high HLB surfactant:low HLB surfactant:oil is about 1.5:0.5:0.4.

Amphoteric Surfactant(s) (Component (c))

The emulsions of the invention include one or more amphoteric surfactant. In an embodiment, these surfactants may be selected, for example, from betaines, sultaines, amphoacetates and amphoproprionates, and mixtures thereof. Preferably the amphoteric surfactant is selected from betaines and amphoproprionates, and most typically betaines.

Betaines which can be used in the current compositions include, for example, coco betaine, cocoamidopropyl betaine, lauryl betaine, laurylhydroxy sulfobetaine, lauryldimethyl betaine, behenyl betaine, capryl/capramidopropyl betaine, and stearyl betaine, and mixtures thereof. In an embodiment coco betaine is used.

Amphoproprionates which can be used in the current compositions include disodium cocoamphodiacetate, cocoamphopropionate, and mixtures thereof.

Sultaines which can be used in the current compositions include cocoamidopropyl hydroxysultaine, lauryl hydroxysultaine, and mixtures thereof.

Amphoacetates which can be used in the current compositions include disodium and sodium amphoacetate, disodium and sodium cocoamphoacetate, and disodium and sodium cocoamphodiacetate, many of which are available for example from Rhodia under the trade name Miranol™, and mixtures thereof.

The one or more amphoteric surfactant is present in the emulsion in an amount from about 3.4% to about 7.4%, preferably from about 4.4% to about 6.4%, most preferably about 5.4%, including all ranges and subranges therebetween, by weight relative to the total weight of the emulsion.

Anionic Surfactant(s) (Component (d))

The emulsions include one or more anionic surfactant. In an embodiment the anionic surfactant is selected, for example, from isethionates, glutamates, alaninates, glycinates, taurates, acyl amino acids, sarcosinates, and alkyl polyglucoside carboxylates, sulfosuccinates, sulfoacetates, and mixtures thereof. More preferably the anionic surfactant is selected from lauryl sulfoacetate, disodium laureth sulfosuccinate, sodium lauryl sulfocacetate, sodium C14-16 olefin sulfonate, and mixtures thereof.

The emulsions of the invention are essentially sulfate-free and preferably contain no sulfates.

The one or more anionic surfactant is present in the emulsion in an amount from about 1.3% to about 2.7%, preferably from about 1.5% to about 2.5%, most preferably about 2%, including all ranges and subranges therebetween, by weight relative to the total weight of the emulsion.

Cationic Polymer(s) (Component (e))

The emulsion of the invention includes one or more cationic polymer. In an embodiment, the cationic polymer may be selected, for example, from cationic homopolymers, cationic copolymers, cationic surfactants and conditioning amines, and mixtures thereof.

Non-limiting examples of cationic polymers include polyquaternium-4, polyquaternium-5, polyquaternium-6, polyquaternium-7, polyquaternium-10, polyquaternium-11, polyquaternium-22, polyquaternium-39, polyquaternium-44, polyquaternium-53 and polyquaternium-67, many of which are available under from Lubrizol (Merquat™), and mixtures thereof.

In a particular embodiment the emulsion includes polyquaternium-10 and polyquaternium-7.

The one or more cationic surfactant is present in the emulsion in an amount from about 0.05% to about 0.6%, preferably from about 0.07% to about 0.3%, most preferably about 0.2%, including all ranges and subranges therebetween, by weight relative to the total weight of the emulsion.

In an embodiment, two cationic surfactants are used at a ratio of from about 0.9:1 to 1:1. In a particular embodiment, these surfactants are preferably selected from polyquaternium-10 (PQ-10) and polyquaternium-7 (PQ-7), the PQ-10 being present in an amount from about 0.05%-0.5%, preferably from 0.09% to about 0.2%, including all ranges and subranges therebetween, and the PQ-7 is present in an amount that is about 10% less than the PQ-10, preferably from about 0.09 to about 0.18, including all ranges and subranges therebetween.

Water (Component (f))

The emulsions according to the invention preferably comprise an amount of water from about 60% to about 95%, more preferably from about 83% to about 87%, including all ranges and subranges therebetween, based on the weight of the final composition.

Optional Additives (if Present, Component (g))

The emulsions according to the invention may also contain additional surfactants, for example olefin sulfonate, sodium sulfate, desyl glucoside, lauryl glucoside, and mixtures thereof. When present, the additional surfactants comprise from about 0.004% to about 1%, preferably from about 0.2% to about 0.6%, in particular about 0.5%, including all ranges and subranges therebetween, of the final composition.

The emulsions may also include any other adjuvant or additive that is usually used in the field of self-cleansing products, in particular shampoos. A person skilled in the art would know which adjuvants and/or additives to select to achieve the desired results (e.g. preservatives) without adversely affecting the properties of claimed emulsions. For example, such additives include preserving agents (e.g. phenoxethanol, sodium benzoate, benzoic acid), sequestrants and chelators (e.g. EDTA, tetrasodium EDTA), consistency regulators (e.g. isopropyl alcohol), thickeners, pH-regulators (e.g. sodium citrate, citric acid), antioxidants, fragrances, dyestuffs such as soluble dyes and pigments, optical brighteners, electrolytes and stabilizers (e.g. sodium chloride, glycerin), and mixtures thereof. Such additives are described, for example in US2012/0308492 at [0079]-[0080] and US2006/0217283 at [0084]-[0087].

In a preferred embodiment the emulsion of the invention also includes at least one salt, and optionally one acid, which typically are present in the aqueous phase. These additives depress the freezing point of the emulsions and generally stabilize the emulsion. They can also be useful as preservatives and clarifiers. Examples of useful salts include sodium chloride, calcium chloride, potassium chloride, magnesium sulfate, and mixtures thereof. Examples of useful acids include benzoic acid and citric acid. When a salt(s) and/or acid(s) is present, it is typically found in an amount from about 1.5% to about 3.5%, in particular 2.0%, including all ranges and subranges therebetween, by weight relative to the total weight of the emulsion.

In another embodiment, water-soluble compounds that decrease the freezing point of the current emulsions may be used to further stabilize the emulsions. Glycerin and sodium chloride are such compounds. When present, such compounds typically are found in an amount ranging from about 1.5% to about 2.5%, particularly 2.0%, including all ranges and subranges therebetween.

When present, the amount of all of these various additives may range, for example from about 0.004% to about 20%, typically from about 0.1 to about 5%, including all ranges and subranges therebetween, by weight relative to the total weight of the emulsion. The additives and the concentrations thereof should be such as not to adversely impact or modify the desired properties of the emulsions of the invention.

The emulsions according to the invention are preferably in a clear liquid form and are optimized for dispensing through a self-foaming pump such as, for example, the pumps sold by Airspray/REXAM PLC, in particular the G3 Cross-section (mm) pump.

EXAMPLES

Preparation

The emulsions of the following examples were prepared as follows:
1. In the main kettle, the following were added: Peg-40 hydrogenated castor oil, Sorbitan oleate, natural oils (olive, coconut and avocado oils), phenoxyethanol, the fragrance, and 5% of water.
2. The contents were stirred with a chopper blade at 200 RPM, heated to 45° C., and homogenized for 2 mins.
3. The remaining water was added.
4. The following were then added with mixing to uniform between additions: Coco-betaine, Sodium lauryl sulfoacetate, Disodium laureth sulfosuccinate, Polyquaternium-10 and Polyquaternium-7. Mix to uniform between additions. The remaining ingredients were added with mixing to uniform.

TABLE 1

| Component | INCI Name | Concentration (%) | | | |
|---|---|---|---|---|---|
| | | Ex 1 | Ex 2 | Ex 3 | Ex 4 |
| (a) (i) | PEG-40 HYDROGENATED CASTOR OIL | 1.5 | 1.5 | 1.5 | 1.5 |
| (a) (ii) | SORBITAN OLEATE | 0.5 | 0.5 | 0.5 | 0.5 |
| (b) | OLIVE OIL | 0.1 | 0.1 | 0.1 | 0.1 |
| (b) | COCONUT OIL | 0.1 | 0.1 | 0.1 | 0.1 |
| (b) | AVOCADO OIL | 0.2 | 0.2 | 0.2 | 0.2 |
| (c) | COCO-BETAINE (30% solution) | 5.4 | 5.4 | 5.4 | 5.4 |
| (d) | SODIUM LAURYL SULFOACETATE | 1 | 1 | | |
| (d) | DISODIUM LAURETH SULFOSUCCINATE | 1 | 1 | 1 | 1 |
| (d) | SODIUM C14-16 OLEFIN SULFONATE | | | | 0.3 |
| (e) | POYLQUATERNIUM-10 | 0.182 | 0.091 | 0.091 | 0.091 |
| (e) | POYLQUATERNIUM-7 | 0.18 | 0.9 | 0.9 | 0.9 |
| (g) | FRAGRANCE | 0.5 | 0.5 | 0.5 | 0.5 |
| (g) | PHENOXYETHANOL | 0.7 | 0.7 | 0.7 | 0.7 |
| (g) | GLYCERIN | | 2 | 2 | 2 |
| (g) | BENZOIC ACID | 0.024 | 0.024 | 0.024 | 0.0255 |
| (g) | SODIUM CHLORIDE | 1.1715 | 3.1715 | 1.1715 | 3.1715 |
| (g) | CITRIC ACID | 0.025 | 0.025 | 0.025 | |
| (f) | WATER | QS (sl* > 87%) | QS (sl* > 83%) | QS (sl* > 85%) | QS (sl* > 83%) |

*"sl >" means slightly greater than.

What is claimed:

1. An oil-in-water emulsion comprising:
    (1) an oil phase comprising:
        (a) from about 1.6% to about 3% of an emulsifying surfactant composition having:
            (i) from about 1.3% to about 2% of one or more first surfactant(s) selected from the group consisting of PEG-40 hydrogenated castor oil, PEG-60 hydrogenated castor oil, PEG-25 hydrogenated castor oil, and mixtures thereof; and
            (ii) from about 0.3% to about 1.0% of one or more second surfactant(s) selected from the group consisting of sorbitan oleate, lecithin, sorbitan monostearate, sorbitan isostearate, sorbitan stearate, oleth-2, sorbitan sesquioleate, and mixtures thereof;
            wherein the ratio of the one or more first surfactant(s) to the one or more second surfactant(s) is between about 2:1 to about 4:1; and
        (b) from about 0.01% to about 1% of one or more non-silicone fatty compound(s); and
    (2) an aqueous phase comprising:
        (c) from about 3.4% to about 7.4% of one or more amphoteric surfactant(s) selected from the group consisting of coco betaine, cocoamidopropyl betaine, lauryl betaine, laurylhydroxy sulfobetaine, lauryldimethylbetaine, behenyl betaine, capryl/capramidopropyl betaine, stearyl betaine, and mixtures thereof;
        (d) from about 1.3% to about 2.7% of one or more sulfate-free anionic surfactant(s) selected from the group consisting of lauryl sulfoacetate, disodium laureth sulfosuccinate, sodium lauryl sulfocacetate, sodium C14-16 olefin sulfonate, and mixtures thereof;
        (e) from about 0.05% to about 0.6% of one or more cationic surfactant(s); and
        (f) from about 60% to about 95% water;
    said emulsion having a viscosity from about 10 cP to about 30 cP;
    wherein all weights are relative to the total weight of the emulsion.

2. The emulsion of claim 1, wherein the one or more non-silicone fatty compound(s) is selected from the group consisting of olive oil, coconut oil, avocado oil, apricot oil, sweet almond oil, castor oil, coriander oil, grapeseed oil, rapeseed oil, hazelnut oil, shea butter, palm oil, apricot kernel oil, rice ban oil, corn germ oil, wheatgerm oil, soybean oil, sunflower oil, evening primrose oil, safflower oil, sesame seed oil, passionflower oil, camellia oil, and mixtures thereof.

3. The composition of claim 1, wherein the one or more cationic surfactant(s) is selected from the group consisting of polyquaternium-4, polyquaternium-5, polyquaternium-6, polyquaternium-7, polyquaternium-10, polyquaternium-11, polyquaternium-22, polyquaternium-39, polyquaternium-44, polyquaternium-53, polyquaternium-67, and mixtures thereof.

4. A clear emulsion of claim 1.

5. A method of cleansing hair comprising contacting the hair with an emulsion of claim 1.

* * * * *